United States Patent [19]
Asselineau et al.

[11] Patent Number: 5,368,691
[45] Date of Patent: Nov. 29, 1994

[54] REACTIVE DISTILLATION PROCESS AND APPARATUS FOR CARRYING IT OUT

[75] Inventors: Lionel Asselineau, Paris; Paul Mikitenko, Noisy le Roi; Jean Charles Viltard, Marly le Roi; Massimo Zuliani, Rueil Malmaison, all of France

[73] Assignee: Institut Francais du Petrole, Rueil-Malmaison, France

[21] Appl. No.: 991,006

[22] Filed: Dec. 16, 1992

[30] Foreign Application Priority Data

Dec. 16, 1991 [FR] France ................. 91 15690

[51] Int. Cl.$^5$ .................. B01D 3/26; C07C 41/06
[52] U.S. Cl. ....................... 203/29; 203/99; 203/DIG. 6; 502/527; 568/699; 568/697; 585/446
[58] Field of Search ............... 203/28, 89, 29, DIG. 6; 202/158; 502/527; 568/699, 697; 585/446, 864

[56] References Cited

U.S. PATENT DOCUMENTS

| | | | |
|---|---|---|---|
| 2,762,683 | 9/1956 | Massey | 23/1 |
| 3,634,535 | 1/1972 | Haunschild | 203/DIG. 6 |
| 4,307,254 | 12/1981 | Smith, Jr. | 568/697 |
| 4,471,154 | 9/1984 | Franklin | 585/864 |
| 4,847,430 | 7/1989 | Quang et al. | 202/158 |
| 4,847,431 | 7/1989 | Nocca et al. | 568/197 |
| 4,950,834 | 8/1990 | Arganbright et al. | 585/446 |
| 5,026,459 | 6/1991 | Quang et al. | 202/158 |
| 5,108,550 | 4/1992 | Piraire et al. | 203/DIG. 6 |
| 5,130,102 | 7/1992 | Jones, Jr. | 203/DIG. 6 |
| 5,236,663 | 8/1993 | Alagy et al. | 203/DIG. 6 |

FOREIGN PATENT DOCUMENTS

2043819 12/1991 Canada .
0461855 12/1991 European Pat. Off. .

*Primary Examiner*—Virginia Manoharan
*Attorney, Agent, or Firm*—Millen, White, Zelano & Branigan

[57] ABSTRACT

A reactive distillation process which makes it possible, in the same enclosure, to carry out a catalytic reaction and isolate by distillation the sought product, in which the liquid phase containing the reagents passes from bottom to top through at least one catalyst bed, without the vapor phase of the distillation traversing said catalyst beds. These operating characteristics occur in a reactive distillation zone (C) including an alternation of distillation cells (D) having one or more trays (5) and reaction cells (R) containing the catalyst beds and designed in such a way that the liquid phase flowing from a distillation tray (5) flows above an overflow (7) through a downpipe (6) and approaches the base of the catalyst bed (8), traverses the latter in a downward flow and is then allowed to flow over a distillation tray (5) of the following distillation cell (D), so that the distillation vapor circulating from bottom to top through the distillation trays (5) does not traverse said reaction cells (R). Each reaction cell (R) is physically separated from the adjacent distillation cell or cells (D). The process can in particular be applied to the synthesis reactions of tertiary alkyl ethers by the addition of aliphatic monoalcohols (methanol, ethanol) on isoolefins (isobutene, isopentene).

9 Claims, 2 Drawing Sheets

REACTIVE DISTILLATION PROCESS AND APPARATUS FOR CARRYING IT OUT

BACKGROUND OF THE INVENTION

The invention relates to a process and an apparatus for performing both chemical reactions and separation by distillation of the reaction mixture obtained. These procedures are known as reactive distillation or catalytic distillation, when the chemical reaction takes place in the presence of a catalyst.

They are more particularly applied to the preparation of tertiary alkyl ethers such as methyl tert. butyl ether (MTBE), methyl tert. amyl ether (TAME), ethyl tert. butyl ether (ETBE) or ethyl tert. amyl ether (TAEE), by catalytic reaction of the appropriate olefin (isobutene or isopentene) with the appropriate alcohol (methanol or ethanol), as a function of the particular case.

They can also be applied to the alkylation of benzene by catalytic reaction with the appropriate olefin, e.g., ethylene or propylene, in order to form the corresponding alkyl benzene, e.g., ethyl benzene or isopropyl benzene.

With more particular regard to the etherification reactions by reactive distillation, various processes have already been proposed in the prior art and in particular in U.S. Pat. No. 3,629,478, EP-A-008860, FR-A-2,503,700 and FR-B-2,628,737.

U.S. Pat. No. 3,629,478 teaches the use of distillation trays and of only loosely placing the catalyst only in the liquid down pipes of said distillation trays, so as to avoid the disturbing effect of the vapour phase through the catalyst. However, the presence of the catalyst in such down pipes leads to a pressure drop, so that the liquid prefers to descend in countercurrent in the orifices provided for the vapor on the work table of each distillation tray, rather than pass through the catalyst, which is consequently placed out of circuit.

The European Patent 0008860 proposes the use of a distillation column filled with an appropriate catalyst for the preparation of methyl tert. butyl ether (MTBE), in which the catalyst also acts as a packing for the distillation, thus forming the MTBE and separating it at the same time from the constituents having four carbon atoms. Although the process described leads to a significant technical contribution in the reactive distillation field, the contact between the liquid phase and the catalyst is intermittent to a varying extent as a result of the disturbing effect of the vapor phase.

The French Patent 2,503,700 proposes the use of a series of catalytic stages with an upward vapor-liquid circulation in the catalyst bed, the catalyst being immersed. However, the distillation effect is not as good as expected. Moreover, a hydrodynamic problem can arise because, due to gravity, it will no longer be easy for the liquid to rise through each catalyst bed.

The French Patent 2,628,737 proposes a technology for bringing about an alternation of the distillation and reaction zones in such a way that in a reaction zone only the liquid phase traverses the catalyst bed in the downward direction. This technology suffers from the disadvantage of requiring, for optimum operation, each distillation zone to have, in addition to one or more conventional distillation trays, a distribution tray and a redistribution tray for the liquid, which increases the height of the column and therefore its costs.

Canadian Patent Application 2,043,819 describes a reactive distillation column having a zone in which are concurrently performed a catalytic reaction and the separation by distillation of the products of said reaction, said zone having reaction "trays" supporting a particulate catalyst and distillation trays, more particularly of the bubble tray type, coupled with the reaction trays by means of a continuous liquid mass immersing, in its lower zone, the said catalyst and, in its upper zone, the said distillation tray. The reaction tray has a stack for supplying the vapor rising from the zone located below the "coupled" assembly to a vapor distributor located below the distillation tray. The height of the liquid mass between the reaction tray and the distillation tray must be adequate to prevent the entrainment of catalyst particles. The liquid phase flows from the upper part of the coupled assembly by flowing over an overflow via a down pipe either to a conventional distillation tray, or to another "coupled" assembly located below the "coupled" assembly in question. In the same way, the reaction tray of a coupled assembly is supplied with liquid phase by a down pipe resulting from flowing over an overflow either from a conventional distillation tray, or from another "coupled" assembly located below the "coupled" assembly in question.

In summarizing, the "coupled" assembly described in this document consists of a bubble tray, in whose bottom is deposited the catalyst, the bubble stack having been extended to take account of the presence of the catalyst mass and its height.

SUMMARY OF THE INVENTION

A process has now been discovered making use of a configuration such that the reaction zones, alternating with the distillation zones, are clearly separated from the latter, i.e., without a continuous liquid mass between a reaction zone and an adjacent distillation zone. Such a configuration makes it possible to get out of the presence of a large liquid mass constituting a significant water hold up, requiring a higher and heavier column, which leads to higher installation costs. Moreover, as will be shown in the following description, the configuration according to the invention allows a greater flexibility in the arrangement of the different zones (reaction and distillation) in the column.

The process and apparatus according to the invention can be applied to various balanced liquid phase reactions, for which it is possible to isolate the reaction product by distillation under the pressure and temperature conditions at which the reaction is performed. Reference can be made, e.g., to the isomerization reactions of paraffins into isoparaffins, the alkylation reactions of aromatic hydrocarbons and the etherification reactions between an isoolefin (e.g., isobutene and isopentene) and an aliphatic monoalcohol (such as methanol or ethanol).

BRIEF DESCRIPTION OF THE DRAWINGS

The process and apparatus according to the invention are described in greater detail hereinafter in conjunction with the drawings, wherein FIG. 1 illustrates diagrammatically the general arrangement of the reactive distillation column, FIGS. 2, 3, 3A and 4 the configuration of the distillation cells and reaction cells at least partly forming a reactive distillation column, according to special, exemplified embodiments, while

DESCRIPTION OF THE PREFERRED EMBODIMENTS

In general terms, the reactive distillation process according to the invention is characterized in that:

the reagents are introduced separately or in mixed form, in pure or diluted form, at at least one level of a reactive distillation column containing:

a) at least one reaction cell containing a bed of the appropriate catalyst for the reaction in question and b) at least one distillation cell constituted by at least one conventional distillation tray, each reaction cell being separated from the adjacent distillation cell or cells by a non-homogeneous interface, the distillation conditions are maintained in the reactive distillation cell, so as to have a liquid phase and a vapor phase in said column, at least part of the liquid phase is circulated upwardly through the catalyst in the reaction cells, at least part of the vapor phase of the distillation is circulated upwardly in such a way that the vapor phase is in contact with the liquid phase in the distillation cells, at least part and preferably almost all the sought reaction product is collected at a single end of the reactive distillation column and generally at the bottom thereof, and in that at least part and preferably almost all the possible diluent of the reagents and the possible excess reagent or reagents are collected at the other end of the column, generally at its top.

Preferably, in the process of the invention, all the liquid phase is circulated upwardly through the catalyst installed in reaction cells.

In preferred manner, all the vapor phase of the distillation is circulated in such a way that it is only in contact with the liquid phase only in the distillation cells and not in the reaction cells.

Figure 1:
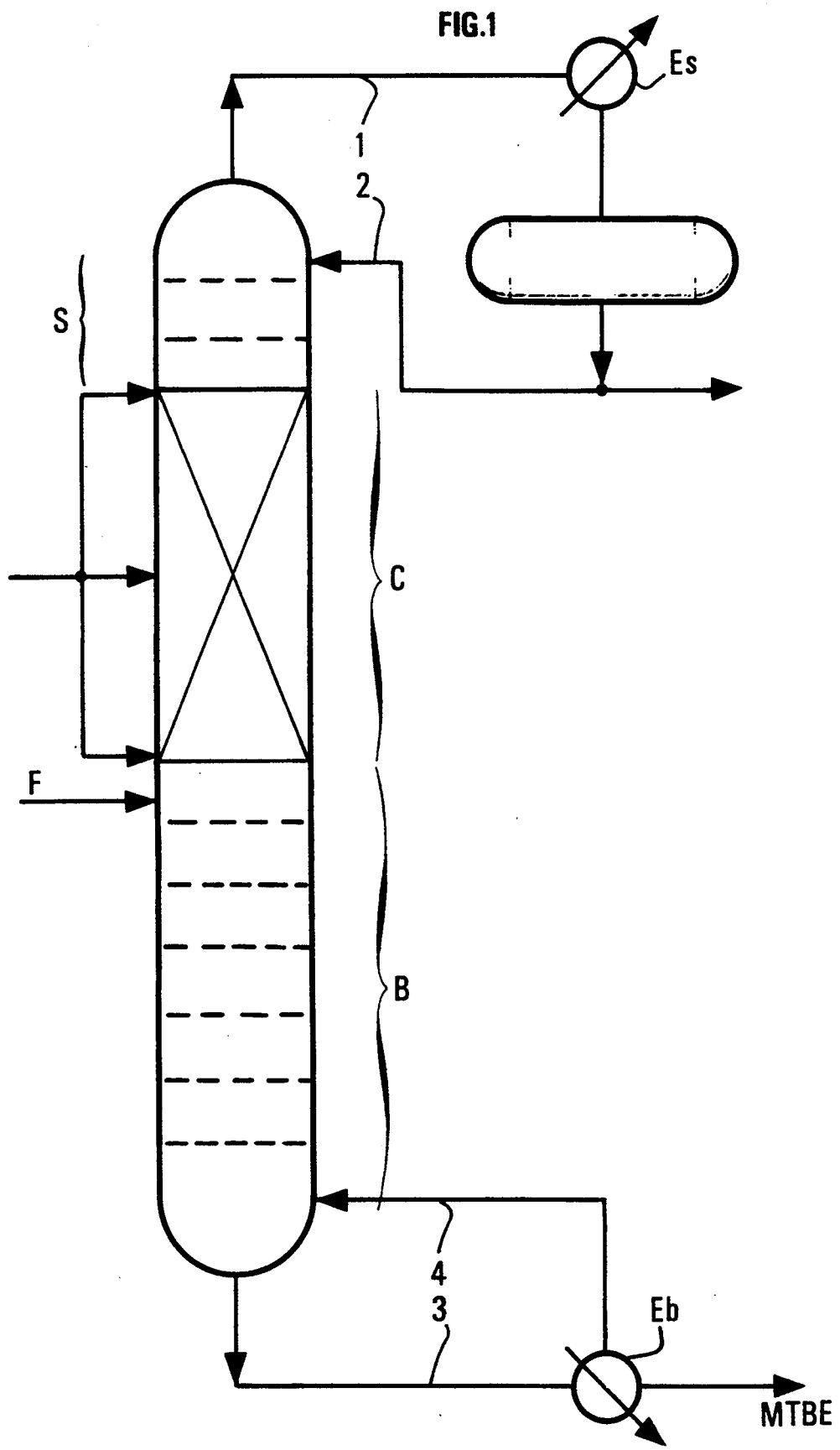
Figure 2:
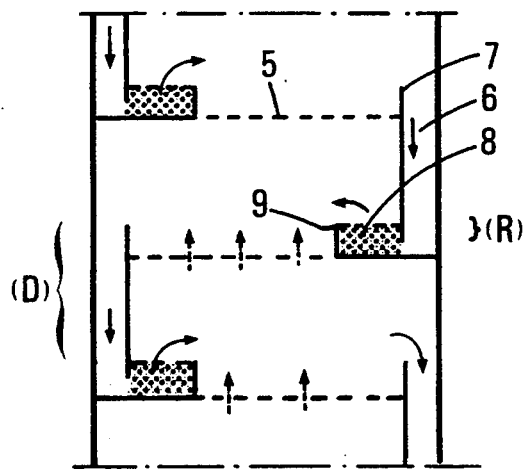
Figure 3:
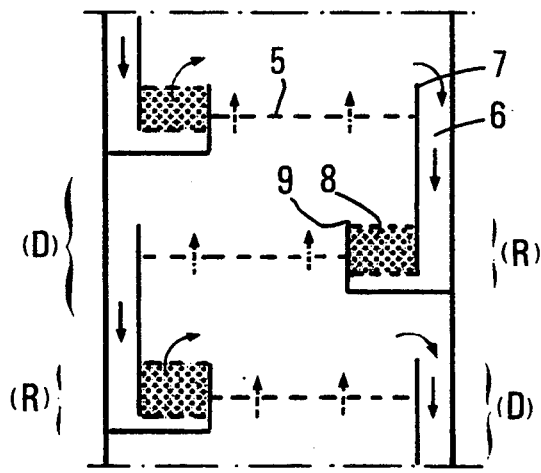

The reactive distillation column used in the process according to the invention essentially comprises three zones, as shown in FIG. 1, namely a catalytic distillation zone (C), in which take place the distillation and chemical reaction, one aiding the other, a top (S) and a base (B).

The column top or head (S) has at least one conventional distillation tray and is being equipped with a pipe 1 for the discharge of the vapors of the most volatile constituents and a pipe (2) for the introduction of a liquid reflux constituted by a fraction of the vapors condensed in the exchanger Es.

In the same way, the column base or bottom (B) has at least one conventional distillation tray and is equipped with a pipe (3) for the discharge of the least volatile constituents in liquid form and a pipe 4 for the introduction of the reboiling vapor produced by the partial vaporization of the bottom liquid in the exchanger Eb. It is also equipped with one or more pipes for introducing all or part of the reagents.

The catalytic distillation zone (C) receives internally a liquid phase produced by the reflux introduced at the top of the column and a vapor phase produced by the reboiling vapor introduced at the base of the column, as well as externally and at at least one level, a possible make up of at least one of the pure or diluted reagents. The paths of the liquid phase and the vapor phase within said catalytic distillation zone are characteristic of the invention. These paths are imposed by the alternating reaction cells (R) and distillation cells (D) within the column. The assembly formed by a reaction cell (R) and an adjacent distillation cell (D) constitutes a "reactive distillation cell".

The reactive distillation cells characterizing the apparatus according to the invention will be described in greater detail relative to FIGS. 2, 3, 3A and 4, which illustrate various embodiments thereof and each of the latter can be chosen as a function of the catalyst quantity to be installed, which is itself determined by the desired conversion for the reagents.

The distillation cells (D) comprise one or more conventional distillation trays, which are chosen from among those known to the Expert and which are in particular perforated trays, bubble trays and valve trays.

In general, each of the said trays comprises (FIGS. 2, 3, 3A or 4): at least one discontinuous worktable, i.e., provided with discontinuities for the passage of the vapor phase, each worktable being used for stirring and mixing the vapor and liquid flows, at least one down pipe (or drain) 6, e.g., located on the edge of each distillation tray, for conditioning the liquid and checking the regularity of its outflow (the liquid previously located on the worktable of said tray flowing down through said down pipe) and at least one overflow (or small curb) 7 bordering each down pipe and designed to maintain a certain liquid level on the worktable of said tray and therefore for checking the regularity of the discharge of the liquid from said worktable.

The reaction cells (R) have a confinement space 8 for the catalyst, designed to be traversed upwardly by the liquid phase without being traversed by the vapor distillation phase, the latter only passing through the distillation cells (D), in which it is contacted with the liquid phase, on each tray.

The catalyst to be installed in all the confinement spaces 8 can be adequately conditioned, particularly in a substantially cylindrical or spherical form, the dimensions of the catalyst particles being variable, e.g., between approximately 0.3 and 20 mm.

In each catalyst bed, the catalyst can be enclosed in one or more liquid-permeable, but catalytic particle-impermeable envelopes (i.e. not permitting the passage of the solid catalyst particles), said envelopes being e.g. constituted by a cloth or crossed wire gauze, largely made from metal.

Figure 5:
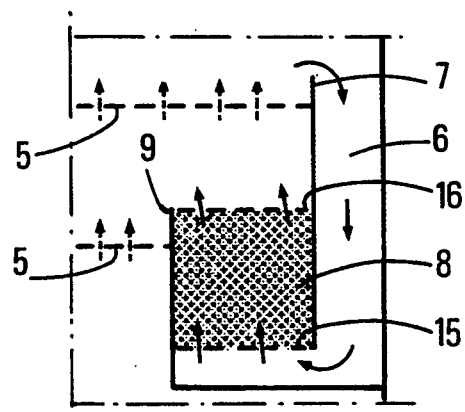
FIG. 5 is a larger-scale view of the catalytic distillation cell of FIG. 3.

The catalyst can also be loosely arranged within each catalyst bed. In this case, in order to keep the catalyst in place and to prevent it being entrained by the liquid flow passing through it, the catalyst bed can be confined between an upper grating 16 and a lower grating 15 having a finer mesh than the smallest catalyst particles. Advantageously, the lower grating 15 is slightly raised with respect to the bottom of the reaction cell (R), so as to permit a better liquid phase distribution, when it approaches the lower part of the catalyst bed and as shown in FIG. 5. When the catalyst is arranged loosely, it can be used in expanded or fluidized form. No matter whether the catalyst is arranged loosely or enclosed in a plurality of envelopes, it could e.g. be given a vacuum level of, e.g., at least $\frac{1}{3}$ and which could rise to $\frac{2}{3}$.

More specifically (FIGS. 2, 3 and 3A), the confinement space 8 for the catalyst of a reaction cell (R) receives the liquid phase containing the reagents flowing out of the lowest distillation tray 5 of the distillation cell (D) located immediately above it by flowing over the overflow 7 and the down pipe 6. In said space 8, through the catalyst bed, the liquid phase moves upwardly and flows over the highest distillation tray 5 of the distillation cell (D) located immediately below it, by flowing over the ledge 9 of said confinement space 8.

In general, the distillation tray 5 of the distillation cell (D), when the latter has one tray, or the highest distillation tray 5 of the distillation cell (D), when the latter has more than one tray, is contiguous with the wall of the confinement space 8 of the reaction cell (R) preceding it in the liquid phase flow. Moreover, the confinement spaces 8 for the catalyst can be designed in such a way that their bottom is at the seine level (FIG. 2) or lower (FIGS. 3 and 3A) than the distillation tray 5 following the same in the liquid flow direction.

In the case where the seine distillation cell (D) has more than two distillation trays (cf. FIG. 3A), each upper tray 5 is connected to the tray 14 immediately below it by at least one down pipe 13. The liquid phase then flows by flowing over the overflow 12. Moreover, in the embodiments described relative to FIGS. 2, 3 and 3A, the vapor phase of the distillation circulating upwardly passes from a distillation cell (D) to the upper distillation cell without encountering any obstacle, the intermediate reaction cell (R), by its confinement space 8, only occupying a small part of the column cross-section.

Figure 4:
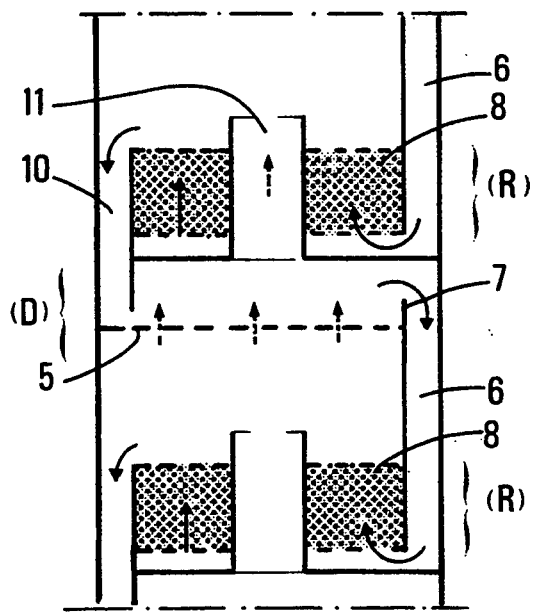
Figure 3A:
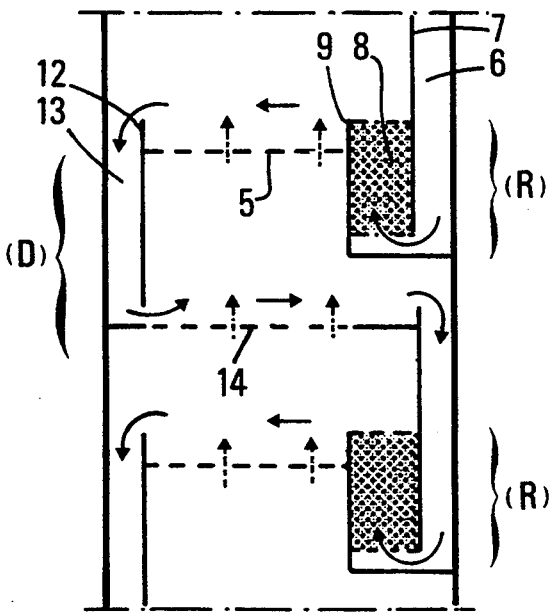

In a different way, in an embodiment like that shown in FIG. 4 where the reaction cells (R) occupy almost all the column cross-sections, the highest distillation tray (5) of the distillation cell (D) following the reaction cell (R) can no longer be contiguous with the wall of its confinement space 8, but must instead be placed below said reaction cell (R) and there is at least one down pipe 10 for the flow of the liquid phase from the reaction cell (R) to the distillation tray 5 and, for the passage of the vapor phase of the distillation, at least one stack 11 positioned through the confinement space 8 of said reaction cell (R). Use is made of such a configuration when it is wished to have a large catalyst quantity in the reaction cells (R).

The essential characteristic of the process and apparatus according to the invention is that each reaction cell is separated from the adjacent distillation cell or cells. The separation by a nonhomogeneous interface is constituted, e.g., in accordance with the arrangement of the reaction cells, by the side wall and/or bottom thereof, which prevent any direct transfer of material between the interior of the reaction cells and the adjacent distillation zones. In particular, said separation implies that there is no continuous liquid junction between the two types of cells.

In the invention, it must be understood that in the sate catalytic distillation zone (C), it is possible to combine the installation of reactive distillation cells of different types as a function of the distillation zone level involved. Thus, for example, it is possible to arrange the catalyst cells like those shown in FIG. 3 in the upper part of the catalytic distillation zone and cells of the type shown in FIG. 4 in the lower part of the same zone.

During the operation of the column, due to the possible entrainment by the liquid of catalyst fines, it can be advantageous to collect on a draw-off tray the liquid flowing out of the reaction cell (R) located at the bottom in the catalytic distillation zone (C), draw off said liquid and filter it in at least one filtering device (positioned outside the column) and reintroduce it into the catalytic distillation column between the position where it was drawn off and the distillation tray located immediately below the draw-off tray. This filtering makes it possible to eliminate all possible catalyst fragments entrained by the liquid phase and in particular prevents them from blocking the bottom of the column.

The process and apparatus according to the invention have the advantage of not requiring the intercalation of liquid redistribution trays between each reaction cell and the lower distillation cell, which leads to a simplification and economy during the construction of columns. Another advantage is that the catalyst is immersed in the liquid and is not disturbed by the vapor phase of the distillation, so that it can operate under optimum efficiency conditions.

Moreover, the use of a rising liquid phase flow through the catalyst beds leads to an expansion and a certain mobility of said beds, as well as the entrainment and discharge of fines with the liquid phase, which avoids the clogging of the catalyst beds. Moreover, in the case of exothermic reactions, e.g., for the synthesis of tertiary alkyl ethers, an advantage of the process according to the invention is that the rising flow of liquid phase through the catalyst beds also makes it possible to easily discharge the vapor phase produced on the catalyst by the reaction heat.

The process and apparatus according to the invention are more particularly applicable to etherification reactions between an isoolefin (e.g., isobutene or isopentene) and an aliphatic monoalcohol (e.g., methanol or ethanol) for the formation of the corresponding ethers. Hereinafter a specific example will be described of application to the synthesis of methyl tert. butyl ether.

The charge containing the isobutene is generally constituted by a $C_4$ fraction obtained from steam cracking, catalytic cracking or dehydrogenation of isobutane. In a first reaction zone, it is contacted with the methanol under well known reaction conditions. This balanced reaction makes it possible to convert part of the isobutene (generally 70 to 90%) into MTBE. It is the mixture from this first zone which is then treated according to the reactive distillation process of the invention.

Working takes place in a column of the type diagrammatically shown in FIG. 1. Generally, the charge F containing the isobutene and methanol which have not been converted is introduced at a level slightly below the actual catalytic distillation zone (C). A make up of methanol generally takes place just above the said zone (C). This make up can also take place at several points along the catalytic distillation zone.

Use is generally made of a sulphonated resin-type catalyst, e.g., a sulfonated divinyl benzene-polystyrene resin, whose grain size is e.g., 0.3 to 1.2 mm. This catalyst is placed in the reaction cells of the column, as described hereinbefore.

The reactive distillation operation is performed under appropriate conditions so that, at the top of the column, the hydrocarbons of the charge which have not reacted pass out through the pipe 1, while the sought methyl tert. butyl ether passes out at the bottom of the column through the pipe 3.

The conditions normally used are a pressure between, e.g., 4 and 16 bars. As a function of the chosen pressure, the temperature at the bottom of the column can be approximately 110° to 170° C. and at the top of the column approximately 40° to 90° C. The reflux rate with respect to the distillate is normally kept at between 0.5:1 and 5:1. This process makes it possible to convert almost all the isobutene and obtain high purity MTBE and in general at least 98 mole %.

EXAMPLE

The following example illustrates the invention and in it the process according to the invention is used for treating a charge from an etherification reactor having the weight composition given in the second column of table 1.

TABLE 1

| Constituent | Charge | Distillate | Residue |
|---|---|---|---|
| Isobutene | 4.6 | 1.4 | <0.02 |
| Butenes | 33.7 | 76.7 | <0.2 |
| Butanes | 8.1 | 18.3 | <0.2 |
| Methanol | 1.4 | 3.6 | — |
| MTBE | 52 | <0.1 | >99 |
| Miscellaneous | 0.2 | — | 0.6 |

Use is made of a 5 cm diameter, 350 cm height stainless steel column. It has an upper zone with seven perforated distillation trays with an overflow, a reactive distillation zone with 12 reactive distillation cells produced according to the principle shown in FIG. 4 and each containing 5 cm$^3$ of a loose catalyst consisting of a sulfonated resin (sulphonated divinyl benzene-polystyrene resin sold by ROHM & HAAS under the registered trademark Amberlyst 15) and a lower zone containing 16 perforated distillation trays with an overflow.

At a flow rate of 1800 g/h, the charge is supplied at the level of the twenty-ninth tray, counted from top to bottom. There is also an injection of a make up of methanol at a rate of 43 g/h to the first reactive tray starting from the top. The column is put into operation at a pressure of 8 bars and with a reflux rate of 1:1 and is regulated in such a way that the distillate discharged consists of inert hydrocarbons in the chemical reaction, together with traces of reagents which have not reacted. Within the column there is a temperature profile from 61° C. at the top to 140° C. at the bottom. At the column head and at a flow rate of 789 g/h is drawn off a distillate having the composition indicated in table 1 and at the bottom and with a flow rate of 1050 g/h, the MTBE produced having the weight composition also indicated in table 1.

We claim:

1. A reactive distillation process comprising:
    reacting, in the presence of a catalyst, at least two reagents, each pure or diluted in at least one diluent to produce one product optionally in admixture with at least one diluent and an excess of at least one reagent, and concurrently separating by distillation said reaction product from the reaction mixture,
    introducing said reagents separately or in mixed form, in at least one level of a reactive distillation column,
    locating at least one reaction cell containing said catalyst as a bed, and
    locating at least one adjacent distillation cell containing at least one distillation tray,
    separating each reaction cell from the adjacent distillation cell by a side wall or bottom of said reaction cell, or both, thereby preventing a direct transfer of matter between the interior of the reaction cells and the adjacent distillation cells,
    maintaining distillation conditions in said column so as to have a liquid phase and a vapor phase therein,
    circulating at least part of the liquid phase upwardly through the catalyst in each reaction cell,
    circulating at least part of the vapor phase of the distillation upwardly through each distillation cell, so that said vapor phase is in contact with the liquid phase only in the distillation cells, and not in the reaction cells,
    collecting at least part of the reaction product at one end of said reactive distillation column and
    collecting at least part of diluent(s) and excess of reagent(s) at the other end of said column.

2. A process according to claim 1, wherein:
    all the liquid phase is circulated upwardly through the catalyst in each reaction cell,
    all the vapor phase of the distillation is circulated upwardly through each distillation cell,
    substantially all product is collected at one end of the reactive distillation column and
    substantially all diluent or excess of reagents is collected at the other end of said column.

3. A process according to claim 1, wherein the reaction is an etherification carried out between an isoolefin and an aliphatic monoalcohol in order to form a tertiary alkyl ether.

4. A process according to claim 3, wherein said isoolefin is isobutene or isopentene and said aliphatic monoalcohol is methanol or ethanol and said tertiary alkyl ether is methyl tert. butyl ether, ethyl tert. butyl ether, methyl tert. amyl ether or ethyl tert. amyl ether.

5. A process according to claim 1, wherein the reaction is alkylation of benzene with ethylene or propylene.

6. A process according to 1, wherein the catalyst is arranged loosely in each reaction cell.

7. A process according to claim 6, wherein a vacuum level of ⅓ to ⅝ is maintained in each reaction cell.

8. A process according to claim 1, wherein the catalyst is enclosed in at least one liquid-permeable, but catalytic particle-impermeable envelope in each reaction cell.

9. A process according to claim 8, wherein the catalyst is expanded in each reaction cell.

* * * * *